US010392513B2

(12) United States Patent
Lischewski et al.

(10) Patent No.: US 10,392,513 B2
(45) Date of Patent: Aug. 27, 2019

(54) SPRAY-DRIED DYE COMPOSITIONS, PROCESS FOR THE PRODUCTION AND USE THEREOF

(75) Inventors: Volker Lischewski, Bitterfeld-Wolfen (DE); Christoph Roth, Halle (DE); Michael Felicetti, Halle (DE); Katrin Schwager, Dessau (DE)

(73) Assignee: Sensient Imaging Technologies GmbH, Bitterfeld-Wolfen (DE)

( * ) Notice: Subject to any disclaimer, the term of this patent is extended or adjusted under 35 U.S.C. 154(b) by 351 days.

(21) Appl. No.: 13/375,542

(22) PCT Filed: Jun. 2, 2010

(86) PCT No.: PCT/EP2010/057744
§ 371 (c)(1),
(2), (4) Date: Oct. 4, 2012

(87) PCT Pub. No.: WO2010/139746
PCT Pub. Date: Dec. 9, 2010

(65) Prior Publication Data
US 2013/0091637 A1    Apr. 18, 2013

(30) Foreign Application Priority Data
Jun. 4, 2009 (DE) .................. 10 2009 026 746

(51) Int. Cl.
| C09B 67/00 | (2006.01) |
| A61K 8/02 | (2006.01) |
| A61K 8/11 | (2006.01) |
| A61Q 19/00 | (2006.01) |
| C09B 63/00 | (2006.01) |
| C09B 67/02 | (2006.01) |

(52) U.S. Cl.
CPC .......... *C09B 67/0097* (2013.01); *A61K 8/025* (2013.01); *A61K 8/0283* (2013.01); *A61K 8/11* (2013.01); *A61Q 19/00* (2013.01); *C09B 63/00* (2013.01); *A61K 2800/412* (2013.01); *A61K 2800/413* (2013.01); *A61K 2800/432* (2013.01); *A61K 2800/56* (2013.01); *A61K 2800/654* (2013.01)

(58) Field of Classification Search
CPC ... C09B 67/0003; C09B 63/00; D06P 1/0016; A61K 8/025; A61K 8/0283; A61K 8/11; A61K 2800/412; A61K 2800/413; A61K 2800/432; A61K 2800/56; A61K 2800/654; A61Q 19/00
USPC ..................................... 8/581, 632, 636, 499
See application file for complete search history.

(56) References Cited

U.S. PATENT DOCUMENTS

| 4,290,811 A * | 9/1981 | Brown ................... C09D 5/106 106/1.17 |
| 2004/0076840 A1* | 4/2004 | Akamatsu ............. C03C 17/002 428/451 |
| 2004/0077757 A1* | 4/2004 | Araki ................... C09D 171/02 524/264 |
| 2008/0176263 A1* | 7/2008 | Schultz et al. .................. 435/23 |

FOREIGN PATENT DOCUMENTS

| WO | WO/2004/081222 A2 | 9/2004 |
| WO | WO/2005/009604 A1 | 2/2005 |
| WO | WO/2006/125661 A1 | 11/2006 |
| WO | WO2009/022307 * | 2/2009 |
| WO | WO/2009/022307 A2 | 2/2009 |

OTHER PUBLICATIONS

International Search Report dated Nov. 16, 2010, Mailed Nov. 25, 2010.

* cited by examiner

*Primary Examiner* — Amina S Khan
(74) *Attorney, Agent, or Firm* — Michael Best & Friedrich LLP

(57) ABSTRACT

The invention relates to spray-dried, washfast dye compositions, preferably in the form of pigment powders, having a bleeding rate of ≤0.5% and consisting of water-soluble functional dyes, preferably food dyes, which are firmly incorporated in a silica matrix. Apart from low bleeding of dye, these compositions are remarkable for their high stability to pH changes and/or ascorbic acid. The invention is also directed to the production of the dye compositions and the use thereof. The dye compositions are preferably employed in coloring foods, cosmetics, pharmaceutical products, but also in other uses.

7 Claims, No Drawings

SPRAY-DRIED DYE COMPOSITIONS, PROCESS FOR THE PRODUCTION AND USE THEREOF

This application is a 371 application of PCT/EP2010/057744 filed Jun. 2, 2010, which claims foreign priority benefit under 35 U.S.C. § 119 of German application 10 2009 026 746.8 filed Jun. 4, 2009.

The invention relates to spray-dried, washfast dye compositions (preferably in the form of pigment powders) having a bleeding rate of ≤0.5% and consisting of water-soluble functional dyes, preferably food dyes, which are firmly incorporated in an organosilane-based silica matrix. Apart from low bleeding of dye, these compositions are remarkable for their high stability to pH changes and/or ascorbic acid. The invention is also directed to the production of the dye compositions and the use thereof. The dye compositions are preferably employed in coloring foods, cosmetics, pharmaceutical products, but also in other uses.

U.S. Pat. No. 6,074,629 or EP 0 581 651 describe processes wherein dyes are encapsulated in a silicon dioxide matrix. However, these processes are essentially based on adsorption of dyes on the matrix surface. Accordingly, the concentration of the dyes inside the matrix is very limited and bleeding is relatively high.

One possible way to reduce bleeding is coating the dye-bearing matrix particles with a second but dye-free matrix which can be made of the same or different material as the core matrix.

For example, the patent document WO 2004/081222 describes the production of pigment particles wherein the aqueous hydrolyzed product of tetraethoxysilane is dyed and emulsified in a water-immiscible liquid. The emulsion is converted into a solid suspension via initiation of a gel-forming process, and the obtained pigment is isolated. The pigment particles are coated with an envelope of dye-free silicon dioxide in a subsequent process step. Bleeding is significantly reduced in this way. However, the coloring effect of such coated pigments is adversely affected by additional reflection and scattering of light on the surface thereof.

Another important property of such dye compositions is their coloring effect on the substrates to be dyed. The dyeing effect of dyes and pigments is tested using coloristic methods, it being well-known that e.g. size and shape of the pigment particles play an important role for the coloristic parameters thereof. The size of the pigment particles should be in the range of 0.05 to 50 µm. The smaller the particles, the better their coloring effect.

To impart clear and deep color to the dyed substrates, it is important that light scattering of the pigment particles is as low as possible. This necessitates a particle shape as spherical as possible. Furthermore, the particles should be transparent to ensure that light can reach the interior thereof so that all dye molecules are struck by the light and can contribute to coloring.

It is of crucial importance that liberation (bleeding) of the per se water-soluble dyes during or after incorporation of the pigments in the substrate to be dyed is as low as possible. In view of the different pH values in coloring uses, the above-mentioned resistance to liberation must be present at all pH values occurring in practice. Another essential requirement is high stability to ascorbic acid (vitamin C). This substance is included in an extraordinarily large number of foods and may give rise to discoloration and decomposition of dyes via a complex chemical mechanism. This must be avoided to the largest possible extent by protecting the dye inside the carrier matrix from the influence of ascorbic acid.

The object of the invention is therefore to provide water-soluble dyes in such a way that they are in an insoluble form, encapsulated in a silicon dioxide matrix, thereby protecting the dyes from bleeding and from the influence of substrate components. The dye compositions in the silicon dioxide matrix should be obtainable in the form of a finely particulate pigment powder. Liberation (bleeding) of free dye from the pigment should be as low as possible and stability to pH and ascorbic acid should be achieved.

According to the invention, said object is accomplished in that a water-soluble dye to be encapsulated is dissolved in a prepared $SiO_x$ sol without using any further additives such as immobilizing or complexing agents. The dyed sol is subjected to a spray-drying process for gelling. Any solvent residues possibly present are removed by secondary drying. Surprisingly, the optionally subsequent temperature treatment can effect a definitely decrease of the dye release (bleeding) from the composition, wherein the temperature treatment is carried out during a time period of at least 2 hours at a temperature of above 50° C.

To produce pigment powders, the gel can subsequently be crushed in a skillful manner.

The process according to the invention effects purely mechanical incorporation in the matrix, so that the relatively large dye molecules are incorporated in the matrix and are prevented from leaving the matrix and/or other organic molecules from entering the same. In this way, bleeding and attack (chemical influence) by ascorbic acid or absorption of incorporated dyes as a result of pH changes can be largely excluded.

The dye compositions thus produced have a bleeding rate of ≤0.5%. Furthermore, they are stable to pH and/or ascorbic acid.

Surprisingly, the only starting materials suitable for the production of the spray-dried, washfast dye compositions according to the invention are alkoxysilane sols which are produced from unsubstituted organosilicon compounds by hydrolysis, preferably heterogeneous catalysis. Hydrolysis of the aqueous-organic alkali silicate solutions is effected at weakly acidic pH values, preferably at pH values of 5.0 to 6.5, particularly at pH values of 5.5 to 6.0. In a particularly preferred fashion, acidification is effected by careful addition of acids. In a particularly preferred embodiment of the invention, hydrolysis is effected in the form of a heterogeneous catalysis, preferably with addition of acidic ion exchangers.

Tetraethoxysilane turned out to be a particularly preferred starting material for the production of the alkoxysilane sol.

Other sources or precursors of a silicon dioxide matrix, e.g. aqueous dispersions of high-purity silicic acid which are obtained by ion exchange of aqueous silicate solutions and include spherical $SiO_2$ particles with a size ranging from 5 to 100 nm, representing so-called nanosols, and are commercially available e.g. under the name of Köstrosol™, are not suitable. As a silica matrix for dye compositions they exhibit major drawbacks with respect to bleeding. The same applies to the use of $SiO_2$ sols produced by catalytic hydrolysis of optionally substituted alkoxysilanes with mineral and organic acids. They exhibit low stability or undesirable discoloration during the production processes.

The $SiO_x$ sols obtained according to the invention can be dyed with one or more water-soluble dyes. Thereafter, the dyed sol is subjected to a conventional spray-drying process. Spray-drying can be performed in any device suitable for spray-drying liquids, e.g. those having at least one spiral-jet spray nozzle or a rotating spray disk, in a preferably heated stream of dry gas such as air or nitrogen.

Single-component, two-component and multi-component nozzles as well as rotating sprayers are suitable in the process as claimed. This process preferably uses concurrent flow spray dryers.

Preferably, the inlet temperature of the stream of dry gas is 80° C. to 250° C., especially 110° C. to 190° C., and the outlet temperature of the stream of gas formed upon drying is 40° C. to 100° C., especially 50° C. to 90° C.

Following spray-drying, any solvent residues possibly present can be removed by a further temperature treatment (secondary drying). The temperature treatment is preferably carried out at a defined temperature above 50° C. and a defined time period of at least 2 hours. The time period can be realized dependent on the dye. As a further result of the second temperature treatment, the structure of the $SiO_x$ matrix is more compact. This additional structure compaction effects a definitely improved decrease of the dye release from the compostion if it is contacted with solvents (especially with water).

Insoluble pigment powders with preferred particle sizes of 0.01 to 100 μm can be provided e.g. by grinding the gel.

According to the invention, natural and synthetic food dyes employed in food products, drugs for oral administration, cosmetic colors or skin care products are preferably envisaged for encapsulation. They can be selected from the following groups:

Brilliant blue (E133; C.I. 42090), tartrazine (E102, C.I. 18140), azorubine (E112; C.I. 14720), EXT. D&C Green No. 1 (C.I. 10020), EXT. D&C Yellow No. 7 (C.I. 10316), EXT. D&C Yellow No. 1 (C.I. 13065), EXT. D&C Orange No. 3 (C.I. 14600), FD&C Red No. 4 (C.I. 14700), D&C Orange No. 4 (C.I. 15510), FD&C Yellow No. 6 (C.I. 15985), D&C Red No. 2 (C.I. 16185), D&C Red No. 33 (C.I. 17200), EXT. D&C Yellow No. 3 (C.I. 18820), FD&C Yellow No. 5 (C.I. 19140), D&C Brown No. 1 (C.I. 20170), D&C Black No. 1 (C.I. 20470), FD&C Green No. 3 (C.I. 42053), FD&C Blue No. 1 (C.I. 42090), D&C Blue No. 4 (C.I. 42090), D&C Red No. 19 (C.I. 45170), D&C Red No. 37 (C.I 45170), EXT. D&C Red No. 3 (C.I. 45190), D&C Yellow No. 8 (C.I. 45350), D&C Orange No. 5 (C.I. 45370), D&C Red No. 21 (C.I. 45380), D&C Red No. 22 (C.I. 45380), D&C Red No. 28 (C.I. 45410), D&C Red No. 27 (C.I. 45410), D&C Orange No. 10 (C.I. 45425), D&C Orange No. 11 (C.I. 45425), FD&C Red No. 3 (C.I. 45430), D&C Yellow No. 11 (C.I. 47000), D&C Yellow No. 10 (C.I. 47005), D&C Green No. 8 (C.I. 59040), EXT. D&C Violet No. 2 (C.I. 60730), D&C Green No. 5 (C.I. 61570) and FD&C Blue No. 2 (C.I. 73015).

Furthermore, the dyes can be selected from a group of natural dyes selected e.g. from grapefruit extract, dyer's safflower extract, cochineal, red beet extract, curcumin, riboflavin, xanthophyll, carotenoids, carmine, carminic acid, anthocyanins, chlorophylls, etc.

The dye compositions according to the invention can be used e.g. as color lake for coloring material surfaces and in the production of indicator strips and sensors. Furthermore, they can be employed as pigment powders dispersed in a polymer binder and as color lake for coloring material surfaces.

In a preferred use the dye compositions can be utilized as pigment powders in dispersed form to dye foods, cosmetic or pharmaceutical preparations or polymer products.

A preferred production process of the dye compositions according to the invention is as follows:

(1) providing an $SiO_2$ nanosol by weak acid hydrolysis of an unsubstituted organosilicon compound, preferably tetraethoxysilane;
(2) admixing the organic dye;
(3) spray-drying;
(4) optionally secondary drying to remove residual solvents, and crushing, e.g. grinding, wherein the secondary drying can be a further defined temperature treatment. This treatment effects a further compaction of the $SiO_x$ matrix.

The temperature treatment following the spray-drying is carried out for several hours, at least 2 hours, at temperatures of from 50° C. to 300° C., preferably at temperatures of from 70° C. to 150° C. The time period of the temperature treatment is preferably carried out from 2 to 120 hours, especially from 5 to 48 hours, optionally in dependency on the selected water-soluble dye.

The pigment powders thus produced have a bleeding of ≤0.5%. Furthermore, they are pH-stable, i.e. the absorptive properties of incorporated dyes will not be affected by changes in pH. In a preferred manner they also show stability to chemical influence of ascorbic acid.

Implementation of the Bleeding Test

Precisely 100 mg of the powdered pigment to be tested is weighed in a 15 ml screw-cap vial using an analytical balance, and precisely 10 ml of a 0.1% solution of Tergitol NP9 (commercially available wetting agent) in distilled water is poured thereon. This mixture is stirred at RT for precisely 1 hour using a small magnetic stirrer. The stirring speed is selected such that all of the powdered material is well agitated. Thereafter, the contents of the vial is sucked into a 10 ml injection syringe (without cannula), a 0.45 μm syringe filter is fitted thereon, and the contents is pressed through the filter and into a second screw-cap vial. The filtrate is subjected to photometry.

Without intending to be limiting, the invention will be explained with reference to the following examples.

EXAMPLE 1

Production of a Blue Color Pigment by Spray-drying a Dyed TEOS Hydrolyzate 20 g of tetraethoxysilane (TEOS) is mixed with 50 g of distilled water, 10 g of ethanol and 4.0 g of glacial acetic acid and stirred vigorously at room temperature using a magnetic stirrer. The TEOS in the liquid initially forms a separate phase (turbid emulsion), but after about 2 hours a clear solution is formed as a result of hydrolysis of TEOS into silicic acid and further condensation to form an $SiO_x$ sol.

0.6 g of FD&C Blue 1 (pure dye) is dissolved in the above solution.

The resulting blue liquid is processed into a powder in a BÜCHI B290 Mini Spray Dryer (inlet temp.=140° C.).

Residual solvents are removed from the powder by secondary drying at elevated temperature.

A pigment with a bleeding rate of 0.01% is obtained.

EXAMPLE 2

Production of a Purple Color Pigment by Spray-drying a Dyed TEOS Hydrolyzate 20 g of tetraethoxysilane (TEOS) is mixed with 4.5 g of distilled water, 10.5 g of ethanol and 5.0 g of 0.001 N HCl and stirred vigorously at room temperature for 48 hours using a magnetic stirrer.

The resulting sol is dyed by adding 3.0 g of Purple Sweet Potato Powder E-500 (20% in maltodextrin), which dye must be completely dissolved by stirring at RT for at least 1 hour.

The dyed sol is immediately processed into a powder in a BÜCHI B290 Mini Spray Dryer (inlet temp.=130° C.).

Residual solvents are removed from the powder by secondary drying at elevated temperature.

The bleeding rate of the obtained pigment is around 0.1%.

EXAMPLE 3

Production of a Blue Color Pigment by Spray-drying a Dyed TEOS Hydrolyzate 20 g of tetraethoxysilane (TEOS) is mixed with 4.5 g of distilled water, 10.5 g of ethanol and 5.0 g of 0.001 N HCl and stirred vigorously at room temperature for 48 hours using a magnetic stirrer.

The resulting sol is dyed by adding 0.6 g of FD&C Blue 1 with stirring and processed into a powder in a BÜCHI B290 Mini Spray Dryer (inlet temp.=130° C.).

The powder is subjected to secondary drying at elevated temperature, thereby removing residual solvents.

The bleeding rate of the obtained pigment is around 0.02%.

EXAMPLE 4

Production of a Blue Color Pigment by Spray-drying a Dyed TEOS Hydrolyzate Produced by Heterogeneous Catalysis 20 g of tetraethoxysilane (TEOS) is mixed with 9.5 g of distilled water, 10.5 g of ethanol and 5.0 g of strongly acidic Dowex HCR-W2 ion exchanger and stirred vigorously at room temperature for 48 hours using a magnetic stirrer.

The resulting sol is filtered from the ion exchanger, dyed by adding and admixing 0.6 g of FD&C Blue 1 and processed into a powder in a BÜCHI B290 Mini Spray Dryer (inlet temp.=130° C.).

Residual solvents are removed from the powder by secondary drying at elevated temperature.

The bleeding rate of the obtained pigment is around 0.01%.

EXAMPLE 5

Production of a Blue Color Pigment by Spray-drying a Dyed TEOS Hydrolyzate and Subsequent Coating with a Dye-Free $SiO_2$ Layer 20 g of tetraethoxysilane (TEOS) is mixed with 4.5 g of distilled water, 10.5 g of ethanol and 1.0 g of glacial acetic acid and stirred vigorously with a magnetic stirrer, starting with 50° C. for 8 hours, followed by room temperature for 96 hours. The resulting sol is dyed by adding and admixing 0.6 g of FD&C Blue 1 and processed into a dry powder in a BÜCHI 8290 Mini Spray Dryer (inlet temp.=140° C.).

Residual solvents are removed from the powder by secondary drying.

The bleeding rate of the obtained pigment is around 0.2%.

5 g of the obtained dry pigment is stirred in 30 g of tetraethoxysilane using a magnetic stirrer and added with 0.3 g of concentrated HCl. The mixture is stirred at RT for 24 hours. Thereafter, the pigment is filtered, washed with water and ethanol and dried.

The bleeding rate is 0.005%.

EXAMPLE 6

Production of a Blue Color Pigment by Spray-drying a Dyed TEOS Hydrolyzate 20 g of tetraethoxysilane (TEOS) is mixed with 50 g of distilled water, 10 g of ethanol and 4.0 g of glacial acetic acid and stirred vigorously at room temperature using a magnetic stirrer. The TEOS in the liquid initially forms a separate phase (turbid emulsion), but after about 2 hours a clear solution is formed as a result of hydrolysis of TEOS into silicic acid and further condensation to form an $SiO_x$ sol.

0.6 g of FD&C Blue 1 (pure dye) is dissolved in the above solution.

The resulting blue liquid is processed into a powder in a BÜCHI B290 Mini Spray Dryer (inlet temp.=140° C.).

The powder is heat-treated using temperature treatment in a drying oven at 110° C. for a time period of 15 hours.

A pigment with a bleeding rate of 0.005% is obtained.

EXAMPLE 7

Production of a Purple Color Pigment by Spray-drying a Dyed TEOS Hydrolyzate 20 g of tetraethoxysilane (TEOS) is mixed with 4.5 g of distilled water, 10.5 g of ethanol and 5.0 g of 0.001 N HCl and stirred vigorously at room temperature for 48 hours using a magnetic stirrer.

The resulting sol is dyed by adding 1.2 g of aqueous elderberry extract (resin-purified, 50% dye content).

The dyed sol is immediately processed into a powder in a BÜCHI B290 Mini Spray Dryer (inlet temp.=130° C.).

The powder is heat-treated using temperature treatment in a drying oven at 140° C. for a time period of 24 hours.

The bleeding rate of the obtained pigment is around 0.05%.

COMPARATIVE EXAMPLE 1

Production of a Color Pigment by Spray-drying a Dyed Köstrosol Solution 45 g of Kostrosol 1520™ (an aqueous liquid containing 20% $SiO_2$, commercially available from Chemiewerk Bad Köstritz, Germany) is added with 50 g of distilled water and 0.9 g of FD&C Blue 1 (pure dye).

The obtained blue liquid is immediately processed into a powder in a BÜCHI B290 Mini Spray Dryer.

Residual solvents are removed from the powder by secondary drying at elevated temperature.

A pigment with a bleeding rate of 7.3% is obtained.

COMPARATIVE EXAMPLE 2

Production of a Color Pigment by Spray-drying a Dyed TEOS Hydrolyzate Obtained by Hydrolyzing with Strong Acid 20 g of tetraethoxysilane (TEOS) is mixed with 10.5 g of ethanol and 9.5 g of 0.1 N HCl and stirred vigorously at room temperature for 24 hours using a magnetic stirrer.

The resulting sol is dyed by adding and admixing 0.6 g of FD&C Blue 1 and processed into a powder in a BÜCHI B290 Mini Spray Dryer (inlet temp.=130° C.).

This powder is subjected to secondary drying at elevated temperature and made free of residual solvents in this way.

The bleeding rate of the obtained pigment is around 0.01%.

Instead of blue, as desired, the color of the powder is green.

The invention claimed is:

1. A process for the production of spray-dried dye compositions comprising water-soluble functional dyes incorporated in an organosilane-based silicon dioxide matrix with bleeding rates of ≤0.5%, comprising the steps of:

a) producing a silicon dioxide sol by weak acid hydrolysis of alkoxysilanes (organosilanes) in an aqueous organic solvent mixture at a pH of 5 to 6.5, wherein hydrolysis is effected by an aqueous acidic ion exchanger and producing the silicon dioxide sol is performed for 48 hours;
b) adding a water-soluble dye;
c) gelling by spray-drying the dyed sol to provide resulting compositions, and
d) temperature treating the resulting compositions for 5 to 48 hours at a temperature above 50° C., wherein the bleeding rate of the dye compositions is measured by contacting a 0.1% aqueous solution of nonylphenol ethoxylate for at least 1 hour with stirring at room temperature.

2. The process according to claim 1, wherein the temperature treatment is carried out at temperatures of from above 50° C. to 300° C.

3. The process according to claim 1, wherein the mixture fed into the spray-drying process contains no further additives.

4. The process according to claim 1, wherein the water-soluble functional dyes are natural or synthetic food dyes used in food products, oral pharmaceutical preparations or cosmetics.

5. The process according to claim 1, wherein the temperature treatment is carried out at temperatures of from 70° C. to 150° C.

6. The process according to claim 1, wherein the dye compositions are further coated with a dye-free $SiO_2$ layer.

7. The process according to claim 1, wherein the temperature treatment is carried out for a time period of 24 hours.

* * * * *